United States Patent
Mlodinow et al.

(10) Patent No.: US 10,363,127 B2
(45) Date of Patent: Jul. 30, 2019

(54) MESH POUCH FOR MEDICAL IMPLANT AND METHOD FOR USING SAME

(71) Applicant: SURGICAL INNOVATION ASSOCIATES, INC., Chicago, IL (US)

(72) Inventors: Alexei Mlodinow, Chicago, IL (US); Stephanie Wiegel, Chicago, IL (US); Todd Cruikshank, Chicago, IL (US)

(73) Assignee: SURGICAL INNOVATION ASSOCIATES, INC., Chicago, IL (US)

( * ) Notice: Subject to any disclaimer, the term of this patent is extended or adjusted under 35 U.S.C. 154(b) by 0 days.

(21) Appl. No.: 16/186,785

(22) Filed: Nov. 12, 2018

(65) Prior Publication Data
US 2019/0142573 A1    May 16, 2019

Related U.S. Application Data

(60) Provisional application No. 62/585,402, filed on Nov. 13, 2017.

(51) Int. Cl.
*A61F 2/12* (2006.01)

(52) U.S. Cl.
CPC ........ *A61F 2/12* (2013.01); *A61F 2210/0004* (2013.01); *A61F 2220/0008* (2013.01); *A61F 2220/0075* (2013.01)

(58) Field of Classification Search
CPC ........................................................ A61F 2/12
USPC ........................................................ 623/7-8
See application file for complete search history.

(56) References Cited

U.S. PATENT DOCUMENTS

| 2,639,035 | A | 5/1953 | Pearlstein |
| 5,383,929 | A | 1/1995 | Ledergerber |
| 5,972,022 | A | 10/1999 | Huxel |
| 6,398,814 | B1 | 6/2002 | Paasimaa et al. |
| 7,875,074 | B2 * | 1/2011 | Chen .................. A61F 2/12 600/37 |
| 9,277,986 | B2 | 3/2016 | Moses et al. |
| 2002/0165596 | A1 | 11/2002 | Wilson |

(Continued)

FOREIGN PATENT DOCUMENTS

| EP | 3191020 A1 | 7/2017 |
| WO | 2016/186803 A1 | 11/2016 |

OTHER PUBLICATIONS

PCT Search Report and Written Opinion issued in related application PCT/US2018/060281, dated Jan. 28, 2019, 10 pages.

*Primary Examiner* — Suzette J Gherbi
(74) *Attorney, Agent, or Firm* — Drinker Biddle & Reath LLP (57) ABSTRACT

An implementation of a mesh pouch includes a mesh wall that defines an enclosure having an opening at an end. The mesh pouch further includes a drawstring configured to close the opening when drawn so as to prevent the surgical implant from leaving the enclosure. The mesh pouch may further include a mesh tab extending from the mesh wall, the mesh tab providing a surface for suturing the mesh pouch to an inner surface of the patient's body. The mesh pouch may further include a strand extending from the mesh wall and a needle attached to a terminus of the strand. The strand may be configured to tighten the mesh wall around the surgical implant when pulled.

18 Claims, 6 Drawing Sheets

(56) References Cited

U.S. PATENT DOCUMENTS

| | | |
|---|---|---|
| 2009/0082864 A1* | 3/2009 | Chen .................... A61F 2/12 |
| | | 623/8 |
| 2010/0217388 A1 | 8/2010 | Cohen et al. |
| 2013/0103149 A1 | 4/2013 | Altman et al. |
| 2014/0350675 A1 | 11/2014 | Hackney et al. |
| 2015/0223928 A1 | 8/2015 | Limem et al. |
| 2015/0250574 A1* | 9/2015 | Egnelov ................ A61F 2/0063 |
| | | 606/151 |
| 2015/0273118 A9 | 10/2015 | Buevich et al. |
| 2015/0351899 A1* | 12/2015 | Mortarino ................ A61F 2/12 |
| | | 623/8 |
| 2017/0224471 A1* | 8/2017 | Rehnke .................... A61F 2/12 |
| 2017/0348084 A1* | 12/2017 | Bowley ................ A61F 2/0063 |

\* cited by examiner

MESH POUCH FOR MEDICAL IMPLANT AND METHOD FOR USING SAME

CROSS-REFERENCE TO RELATED APPLICATIONS

The present application claims the priority benefit of U.S. Provisional Patent Application 62/585,402, filed on Nov. 13, 2017 and incorporated herein by reference in its entirety.

TECHNICAL FIELD

The present disclosure relates generally to mesh coverings for implants and, more particularly, to a mesh pouch for an implant and method for using same.

BACKGROUND

The present disclosure relates to field of surgically implantable devices. Aspects of this disclosure specifically relate to the support and stabilization of a breast prosthesis using bioabsorbable, flexible mesh pouches.

Synthetic implants composed of silicone or saline are commonly used in both breast augmentation and reconstruction, but in both cases the soft tissue envelope alone is sometimes insufficient to keep the implant in the appropriate location. Further, in many cases it is difficult to achieve or maintain an anatomically appropriate breast shape when a round implant is used. Due to these deficiencies in native tissue, a revision surgery is sometimes needed to reshape, reposition, lift, or otherwise modify the implant and/or periprosthetic tissue. A revision surgery could be avoided if an additional, shaping, localizing support structure for the breast implant was provided. An internal bra in a sling or a hammock configuration is sometimes used to provide additional support for the breast implant over time. Common materials for the internal bra hammock are surgical mesh and decellularized tissue.

These internal bras provide additional support for the breast implant, but improved support and stabilization are still needed to ensure long-lasting results in breast augmentation and reconstruction procedures.

DRAWINGS

While the appended claims set forth the features of the present techniques with particularity, these techniques may be best understood from the following detailed description taken in conjunction with the accompanying drawings of which:

DETAILED DESCRIPTION

The disclosure is generally directed to a mesh pouch for securing an implant with a patient's body. According to various embodiments, the mesh pouch includes a mesh wall that defines an enclosure having an opening. The mesh pouch further includes a drawstring configured to close the opening when drawn so as to prevent the surgical implant from leaving the enclosure. The mesh pouch may further include a mesh tab extending from the mesh wall, the mesh tab providing a surface for suturing the mesh pouch to an inner surface of the patient's body. The mesh pouch may further include a strand extending from the mesh wall and a needle attached to a terminus of the strand. The strand may be configured to tighten the mesh wall around the surgical implant when pulled.

The mesh pouch disclosed herein provides extra support and stabilization. After the implant is inserted into the mesh pouch and the tabs are sutured to the chest wall, the 360 degree mesh enclosure keeps the implant localized for the duration of the healing process and alleviates the surrounding soft tissues of the weight of the implant. This latter benefit is particularly advantageous in post-mastectomy breast reconstruction, which is commonly performed in a setting of tenuous blood supply to the skin flaps that remain. The tabs on the outside wall of the mesh pouch provide additional surface area to suture and support the encased breast implant, without running the risk of puncturing the implant by suturing directly through the outer wall of the pouch. Compared to the hammock method, which only provides support and localization in the cranio-caudal plane, the pouch method described herein can fully bear the weight of the implant, force the implant into the desired shape, and keep the implant localized medio-laterally. Further, it is more time-efficient to put an implant into a pre-shaped pouch, cinch it closed, and suture a small number of tabs in place than it is to cut a custom hammock or sling out of a flat sheet, and then tailor it into the hemi-pocket of the appropriate size and shape for the given implant and soft tissue deficit.

Various embodiments of the mesh pouch include one or more drawstrings around an opening, which can be pulled to close the opening. Using a drawstring design allows the walls of the mesh pouch to fit flush against an implant. This design helps to eliminate bunched up material and resulting air pockets, which can cause bacterial infection, and swelling.

Embodiments of the mesh pouch described herein have no resorbable coating. Instead, embodiments described herein are completely constructed of a bioabsorbable material. Having the entire device constructed from a bioabsorbable material can cut down on complications and infections commonly seen from a non-bioabsorbable mesh implant.

The various embodiments described herein provide patients with longer-lasting results from breast augmentation or reconstruction, which reduces the need for subsequent revision surgeries.

Turning to FIGS. 1-4, a mesh pouch according to an embodiment is illustrated. The mesh pouch, generally labeled 100, includes a mesh wall 102 that surrounds and defines an enclosure 104. The mesh wall 102 is spheroid in shape when fully expanded, but is configured to conform to the shape of an implant when in use. The mesh wall 102 has an opening 106 at an end 108, through which an implant (such as a breast implant or other mammary prosthesis, such as a tissue expander) may be inserted.

In an embodiment, the mesh wall 102 is made up of a first series of circular cords 110 that surround a longitudinal axis A of the mesh pouch 100, and which are smallest in circumference at opposite ends 108 and 112 of the mesh pouch 100 and largest in circumference around the center 114 of the mesh pouch 100. The mesh wall 102 is further made up of a second series of circular cords 116, which are oriented in planes that are perpendicular to the planes of orientation of the first series circular cords 110. The mesh wall 102 is still further made up of a third series of circular cords 118, which are oriented in planes that are perpendicular to the planes of orientation of both the first set of circular cords 110 and the second series of circular cords 116. The second and third series of circular cords 116 and 118 are discontinuous in places where the opening 106 interrupts them.

In an embodiment, the mesh wall 102 comprises a porous material, such as knitted surgical mesh. It is configured to maintain a three-dimensional configuration, such as a breast-shape or a sphere-shape, independent of the presence of a surgically-implanted device. It may be made of a stretchable material that allows expansion of the opening 106 and subsequent contraction of the opening 106 to or near its original size. The mesh wall 102 may be made of a bioabsorbable material such as poly-(p)-dioxanone, poly-trimethylene-carbonate, polyglycolide, etc. It may also be composed of a biologic material. including complex extracellular matrices and simple polymers such as P4HB, fibroin, etc.

Figure 1:
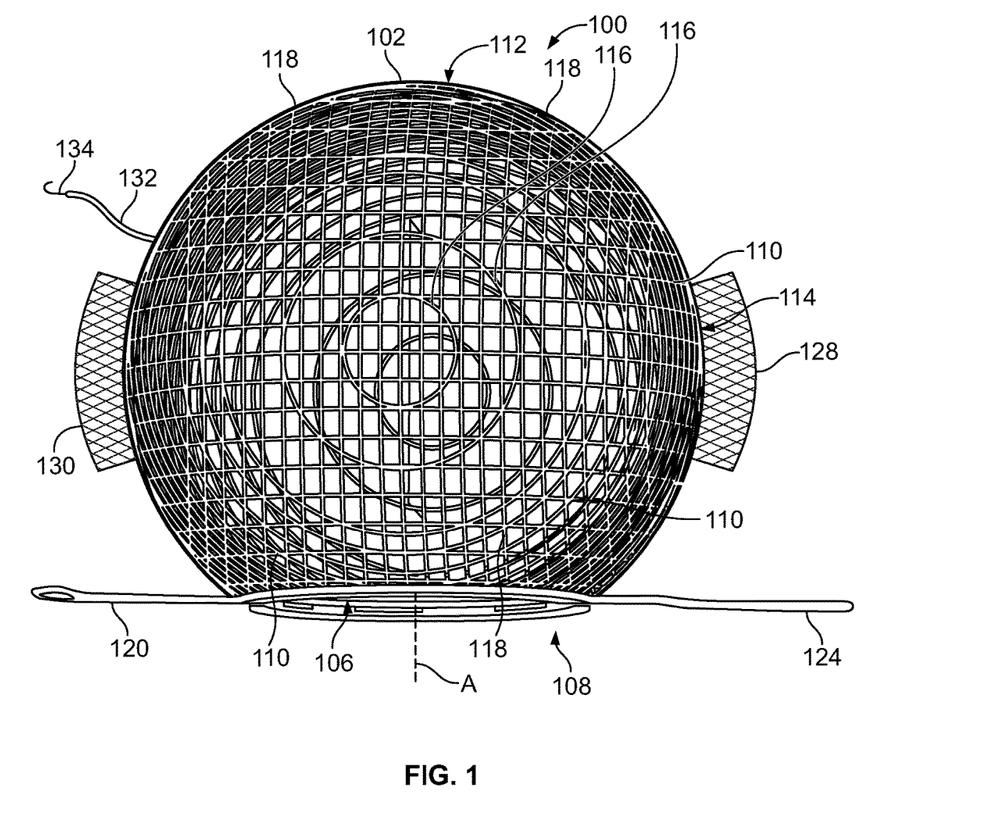
FIG. 1 is a top view of a mesh pouch configured in accordance with an embodiment.
Figure 2:
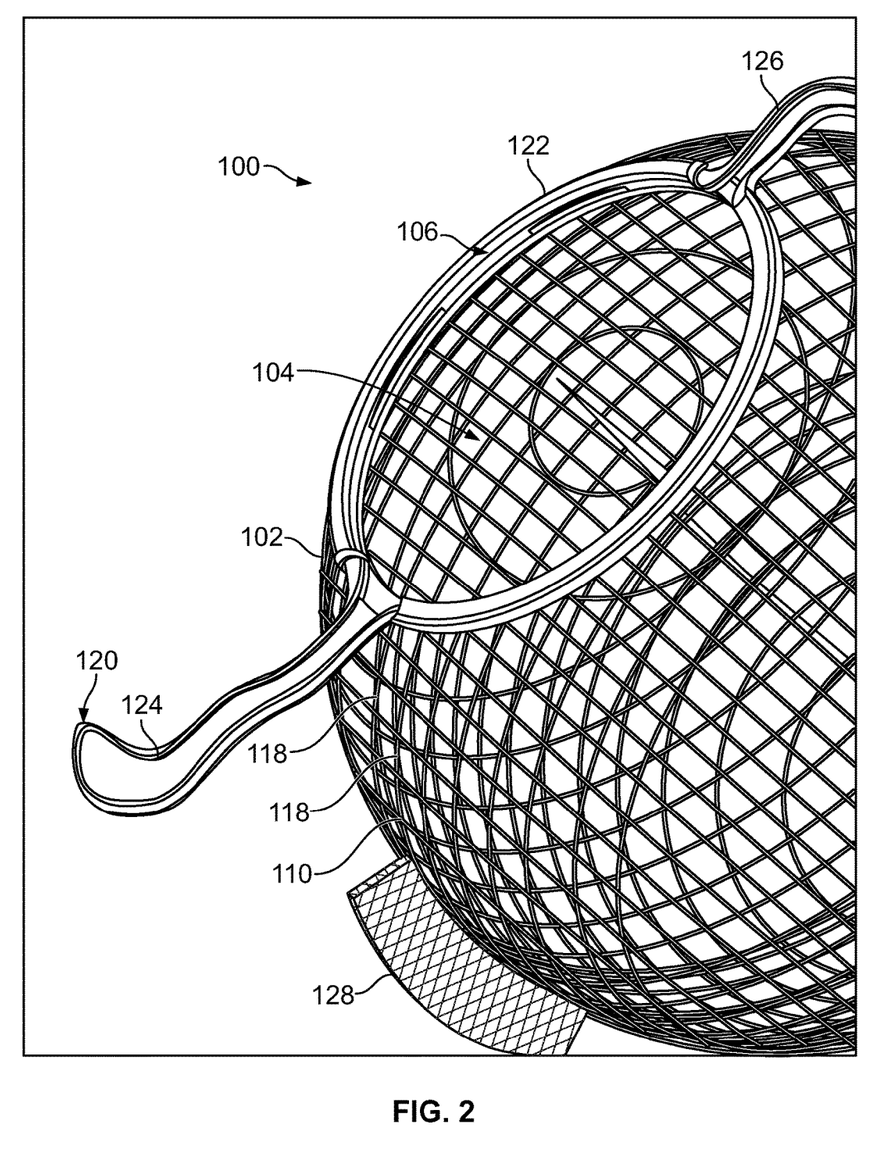
FIG. 2 is a perspective close-up of an opening of the mesh pouch along with a drawstring.
Figure 3:
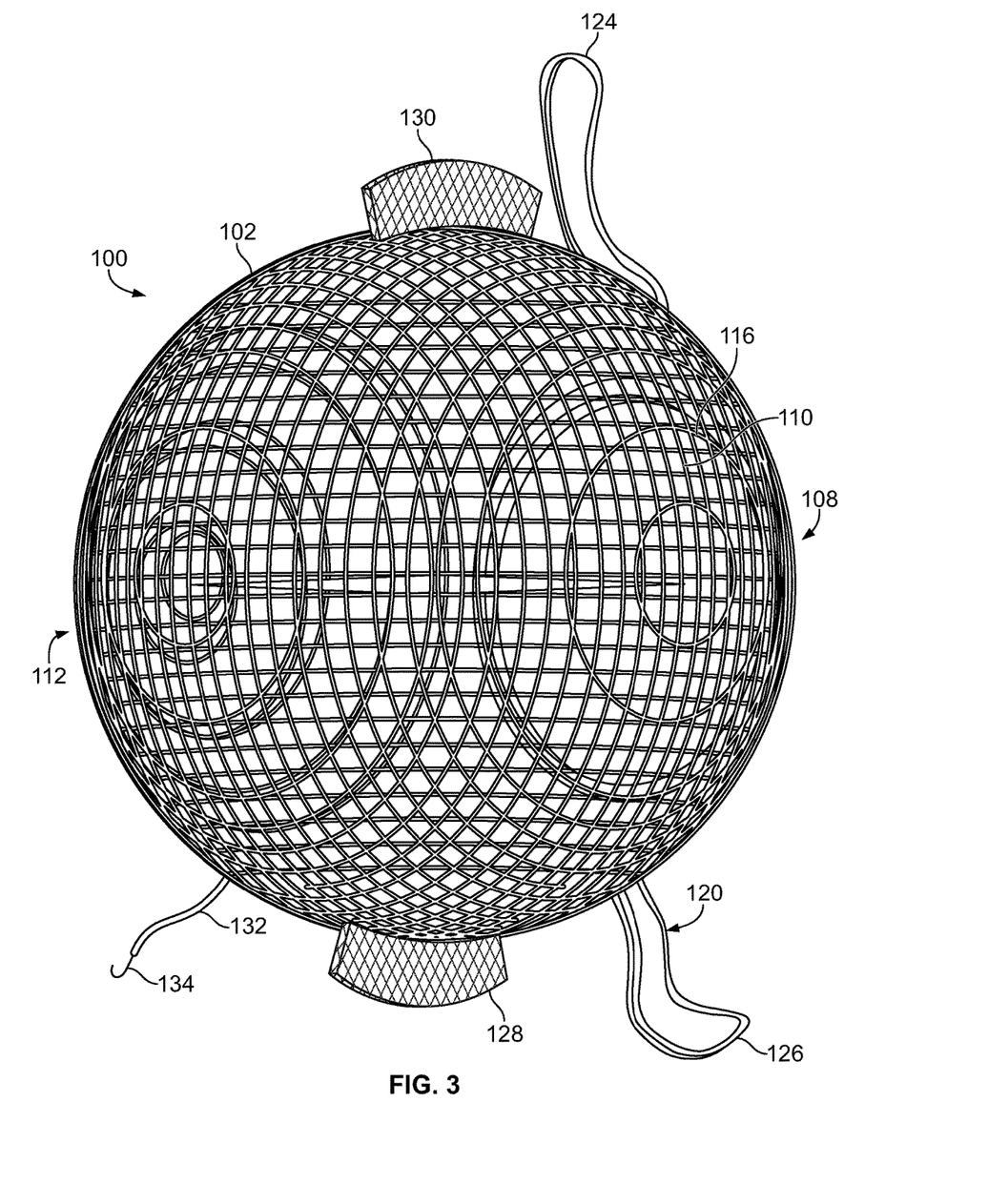
FIG. 3 is a perspective rear view of the mesh pouch.
Figure 4:
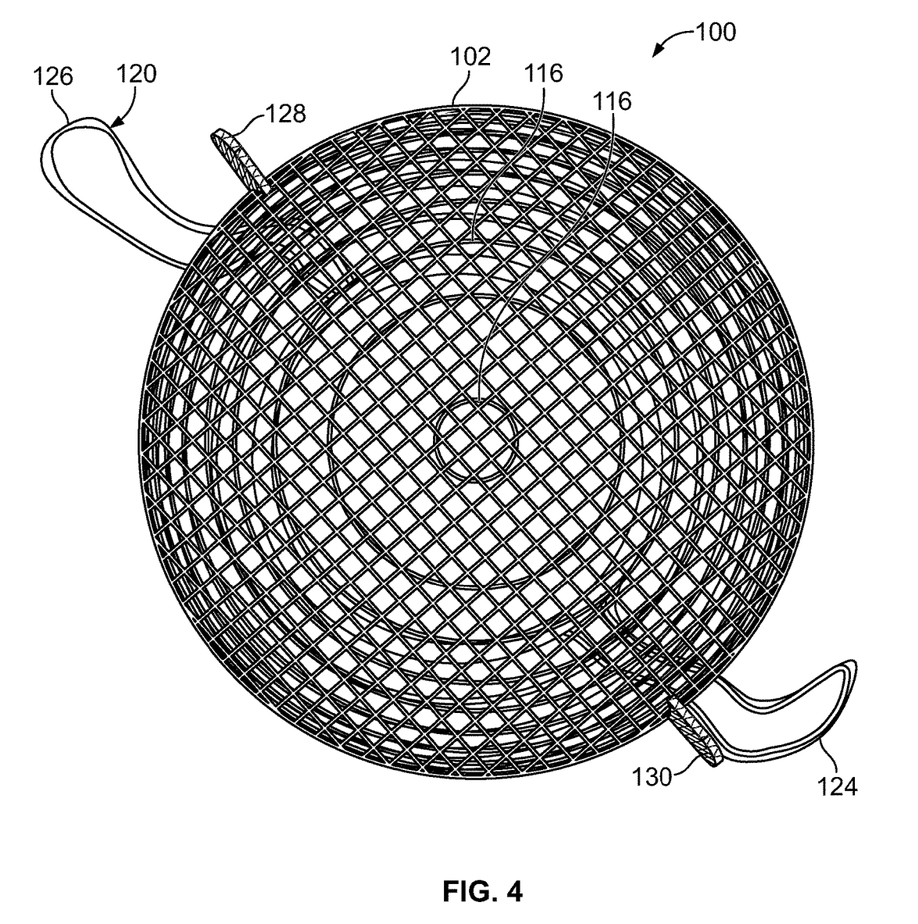
FIG. 4 is a rear view of the mesh pouch.

According to an embodiment, proximate to and surrounding the opening 106 is a drawstring 120 which, when pulled away from the mesh wall 102, closes the opening 106 sufficiently to prevent an implant from leaving the enclosure 106. Turning to FIG. 2, the drawstring 120 is secured to the mesh wall 102 by a sleeve 122 (which may be made of solid material or may be made of a series of threaded loops). The drawstring 120 has a first free portion 124 and a second free portion 126, each of which is free from the sleeve 122. In order to close the opening 106, one or both of the free portions 124 and 126 are pulled away from the mesh wall 102. Instead of a sleeve 122, the drawstring 120 may be attached to the mesh wall 102 via one or more openings along the edge of the opening 106 (e.g., sufficiently dimensioned so that a cord or string can be passed through and pulled to close the opening of the pouch in a drawstring or purse string fashion).

In an embodiment, material around the opening 106 has elastic properties conferred by the textile characteristics of the mesh wall 102 (e.g., at the rim of the opening) such that a surgical implant may be placed in the enclosure 106 by forcibly widening opening and inserting the implant. The implant is then trapped by the retraction of the opening. This embodiment may or may not include a drawstring.

As shown in FIGS. 1-4, in an embodiment, the mesh pouch 100 includes one or more extensions, shown in the figures as a first mesh tab 128 and a second mesh tab 130. The mesh tabs 128 and 130 are attached to the mesh wall 102 on opposite sides of the widest point of the mesh pouch 100. The mesh tabs 128 and 130 provide surfaces for suturing the mesh pouch 100 to interior portions (e.g., internal tissue) of a patient. The pore sizes and pattern of the mesh tabs may vary depending on the embodiment. Two mesh tabs are shown in the drawings, but additional mesh tabs are possible in other embodiments. In this embodiment the mesh tabs 128 and 130 are placed on the same plane halfway (or approximately halfway) through the cross of the spheroid shape of the mesh pouch 100. Other embodiments may have the mesh tabs placed on different planes or at different cross-sectional lengths along the diameter of the mesh pouch.

In an embodiment, the mesh pouch 100 includes an integrated strand 132 attached to the mesh wall 102. The strand 132 has a needle 134 attached to its terminus. The strand 132 may be used to suture the mesh pouch 100 to an interior portion of a patient. According to an embodiment, the strand 132 is connected to one or more of the cords of the mesh wall 102 (either with a sleeve configuration such as the drawstring 120 or without a sleeve) so that pulling the strand 132 (e.g., while suturing using the strand) has the effect of making the enclosure 104 smaller so that the mesh wall 102 fits more snugly onto an implant. The mesh pouch 100 may have multiple such integrated strands with needles.

Figure 5:
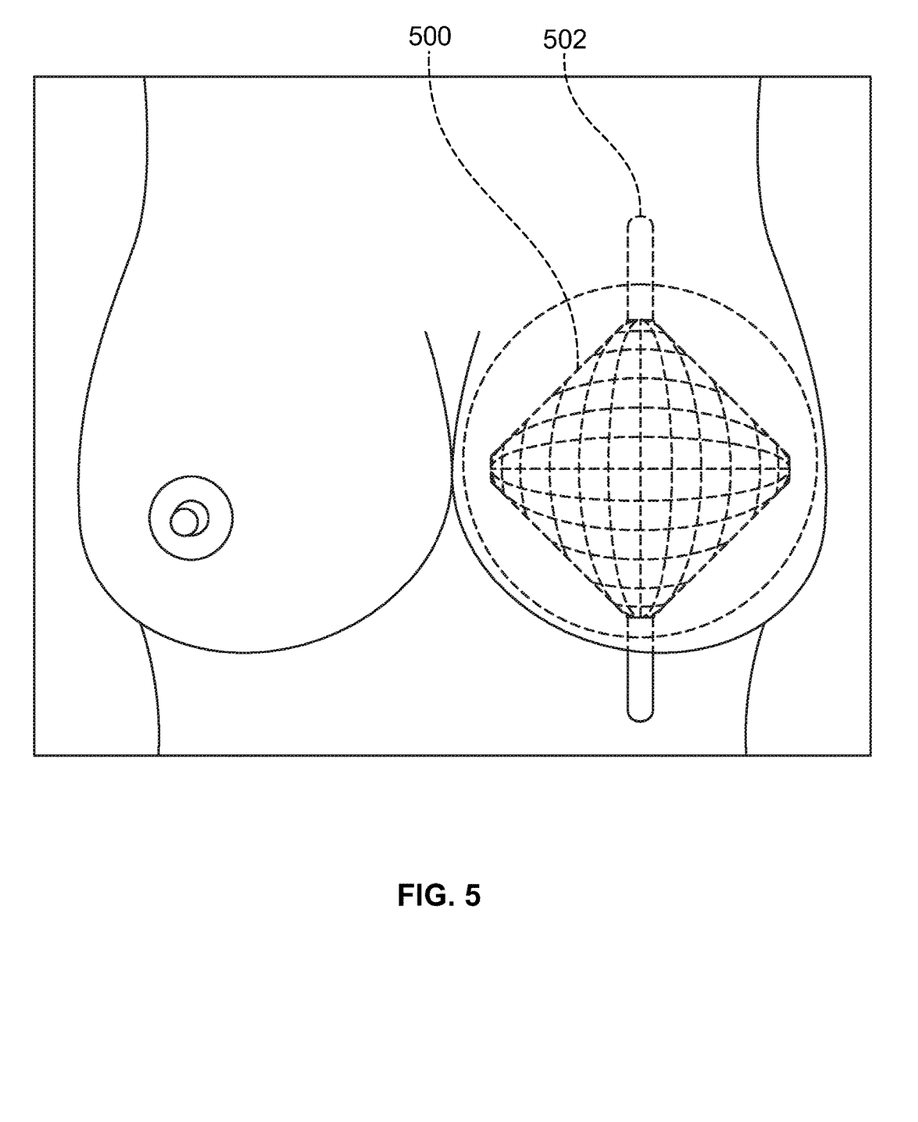
FIG. 5 and FIG. 6 depict a method for using the mesh pouch in surgery, according to an embodiment.
Figure 6:
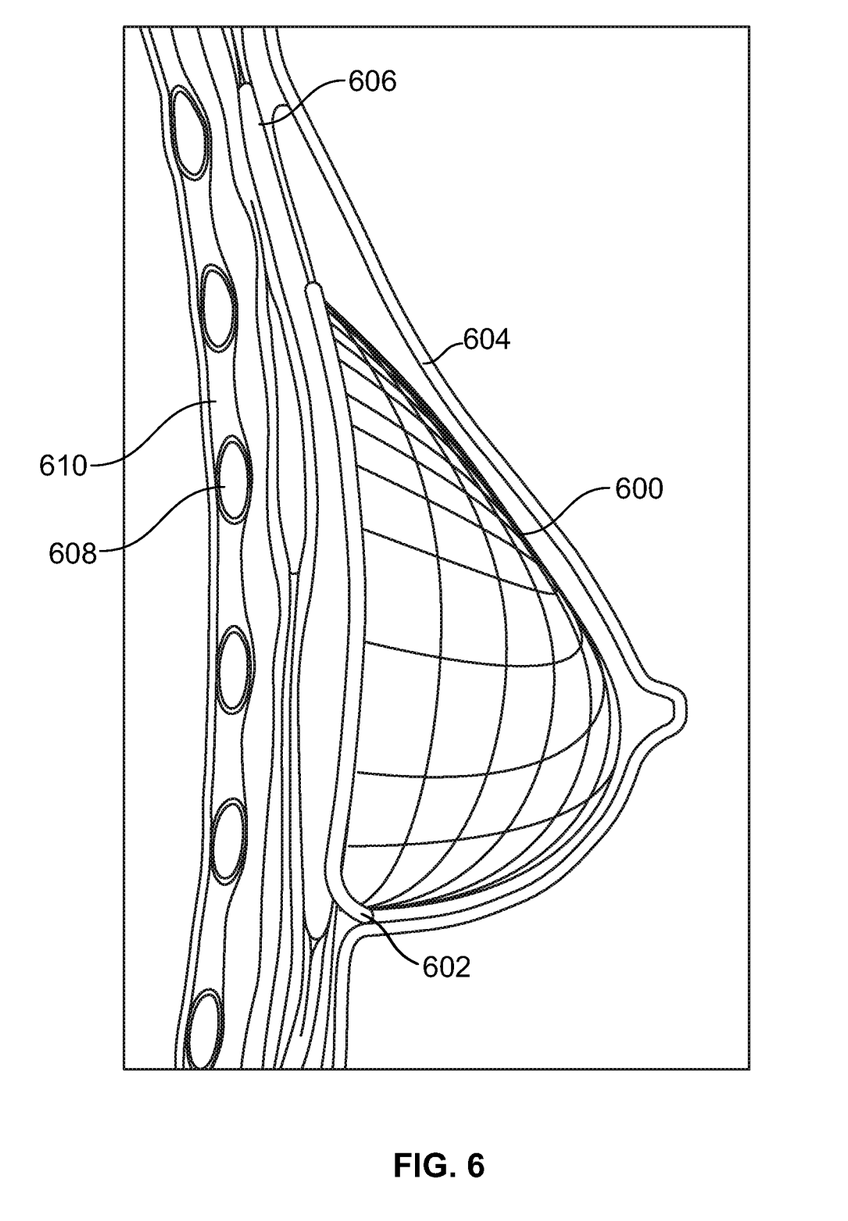

Turning to FIG. 5 and FIG. 6, an example of how the mesh pouch 100 is used will now be described. A medical device, such as a breast implant is inserted into the mesh pouch 100 through the opening 106. After the medical device is inserted it will be fully encased inside the mesh wall 104. The drawstring 120 is pulled such that the opening 106 becomes increasingly small as the drawstring 120 is pulled tighter until it is tight. The drawstring 120 is then cinched. The implant may be held within the mesh pouch 100 due to the elastic recoil of the mesh wall 102, or more firmly by closure of opening 106 with the drawstring 120. The resting shape of the mesh wall 102 may force a round implant enclosed in this way to take on a more natural breast shape.

The implant within the mesh pouch 100 can then be placed in the appropriate position and appropriate tissue plane as it would be without the mesh pouch 100 (between the skin and the pectoralis/fascia in the setting of prepectoral breast reconstruction, for example). However, after placement, the integrated mesh tabs 128 and 130 can be sutured directly to the soft tissue (an interior the chest wall or other tissue, such as the pectoralis fascia, for example) in order to maintain its position during the healing process. The suturing of the mesh pouch 100 to the chest wall provides a way to localize the implant without having to rely on soft tissue manipulation, and the position of the tabs distant from the breast prosthesis minimizes the risk of accidental damage to the breast prosthesis during this process. Positioning and shaping may be further facilitated by the use of the integrated needle 134 (or needles, if there are multiple) to suture to the chest wall, which (if integrated with the mesh wall 102 as described above) also cinches down or tailors the mesh pouch 100 as desired by the tightening of strands (e.g., integrated fibers) to which the integrated needles are attached. Finally, the overlying layers (skin and subcutaneous tissue, for example), are closed. The weight of the implant is borne by the mesh pouch 100 and the soft tissue to which it is sutured, rather than the skin envelope that is covering it.

According to an embodiment, the mesh pouch 100 is formed as follows: 1) A mesh sheet is formed by warp knitting, electrospinning, or other textile technique. 2) A thermally conductive mold or mandril is formed in a desired spheroid or breast shape. 3) The mesh is wrapped around and annealed to the mold or mandril to the desired spheroid or breast shape.

The mesh pouch 100 may have uses in multiple domains of breast surgery, such as direct-to-implant, prepectoral, breast reconstruction for a mastectomy defect. In this setting, recreation of the breast mound is performed by placing a prosthetic breast implant in the plane between the pectoralis muscle and the overlying skin, in the space where breast tissue used to reside prior to the mastectomy. For example, in FIG. 5, there is depicted a mesh-pouched implant 500 (configured according to one or more of the previously described embodiments) disposed in situ in a human breast, with a retractor 502 also shown. In FIG. 6, there is depicted a mesh-pouched implant 600 (configured according to one or more of the previously described embodiments) disposed in situ in a human breast with a mesh tab 602 sutured in place. The various tissue shown in FIG. 6 includes skin and subcutaneous tissue 604, pectoralis 606, ribs 608, and intercostals 610.

It should be understood that the embodiments described herein should be considered in a descriptive sense only and not for purposes of limitation. Descriptions of features or aspects within each embodiment should typically be considered as available for other similar features or aspects in other embodiments. It will be understood by those of ordinary skill in the art that various changes in form and details may be made therein without departing from their spirit and scope.

What is claimed is:

1. A mesh pouch for holding a surgical implant within a patient's body, the mesh pouch comprising:
    a mesh wall that defines an enclosure having an opening at an end of the enclosure;
    a drawstring configured to close the opening when drawn so as to prevent the surgical implant from leaving the enclosure; and
    a mesh tab extending from the mesh wall, the mesh tab providing a surface for suturing the mesh pouch to an inner surface of the patient's body.

2. The mesh pouch of claim 1, further comprising a strand extending from the mesh wall.

3. The mesh pouch of claim 2, further comprising a needle attached to a terminus of the strand.

4. The mesh pouch of claim 1, further comprising one or more strands extending from the mesh wall, wherein each of the one or more strands is configured to tighten the mesh wall around the surgical implant when pulled.

5. The mesh pouch of claim 1, wherein the mesh wall comprises a series of circular cords that surround a longitudinal axis of the mesh pouch.

6. The mesh pouch of claim 5, wherein the mesh wall further comprises a second series of circular cords oriented in planes that are perpendicular to planes of orientation of the series of circular cords.

7. The mesh pouch of claim 1, wherein the enclosure is spheroid in shape when the mesh wall is fully expanded.

8. The mesh pouch of claim 1, wherein the mesh wall is made of a stretchable material that allows the expansion and contraction of the opening.

9. The mesh pouch of claim 1, wherein the mesh wall is made of a material selected from a group consisting of poly-(p)-dioxanone, poly-trimethylene-carbonate, polyglycolide, P4HB, and fibroin.

10. A method for securing a surgical implant in a patient's body, the method comprising:
    inserting the implant through an opening of a mesh wall of mesh pouch, the mesh wall defining an enclosure;
    drawing a drawstring proximate to the opening to close the opening, thereby preventing the implant from leaving the enclosure;
    inserting the mesh pouch into a patient's body; and
    suturing the mesh pouch to tissue within the patient's body.

11. The method of claim 10, wherein suturing the mesh pouch comprises suturing a mesh tab extending from the mesh wall to the tissue.

12. The method of claim 10, wherein suturing the mesh pouch comprises suturing a strand extending from and integrated with the mesh wall to the tissue, thereby tightening the pouch around the implant.

13. A mesh pouch for holding a surgical implant within a patient's body, the mesh pouch comprising:
    a mesh wall that defines an enclosure having an opening at an end of the enclosure;
    a drawstring surrounding a rim of the opening and configured to close the opening when drawn so as to prevent the surgical implant from leaving the enclosure;
    a strand extending from the mesh wall; and
    a needle attached to a terminus of the strand.

14. The mesh pouch of claim 13, wherein the mesh wall comprises a series of circular cords that surround a longitudinal axis of the mesh pouch.

15. The mesh pouch of claim 14, wherein the mesh wall further comprises a second series of circular cords oriented in planes that are perpendicular to planes of orientation of the series of circular cords.

16. The mesh pouch of claim 13, wherein the enclosure is spheroid in shape when the mesh wall is fully expanded.

17. The mesh pouch of claim 13, wherein the mesh wall is made of a stretchable material that allows the expansion and contraction of the opening.

18. The mesh pouch of claim 13, wherein the mesh wall is made of a material selected from a group consisting of poly-(p)-dioxanone, poly-trimethylene-carbonate, polyglycolide, P4HB, and fibroin.

* * * * *